United States Patent [19]
Catlow et al.

[11] Patent Number: 5,798,367
[45] Date of Patent: Aug. 25, 1998

[54] INDAZOLECARBOXAMIDES

[75] Inventors: John T. Catlow, Indianapolis; Marlene L. Cohen, Carmel; Michael J. Martinelli, Indianapolis; John M. Schaus, Zionsville; Steven Swanson; Dennis C. Thompson, both of Indianapolis; Thomas M. Wilson, Speedway, all of Ind.

[73] Assignee: Eli Lilly and Company, Indianapolis, Ind.

[21] Appl. No.: 781,421

[22] Filed: Jan. 10, 1997

Related U.S. Application Data

[60] Division of Ser. No. 485,956, Jun. 7, 1995, Pat. No. 5,654,320, which is a continuation-in-part of Ser. No. 405,119, Mar. 16, 1995, abandoned.

[51] Int. Cl.$^6$ .................................................. A61K 31/445
[52] U.S. Cl. .................. 514/322; 514/212; 514/234.5; 514/255; 514/307; 514/403
[58] Field of Search .................. 514/212, 234.5, 514/255, 322, 307, 403; 540/603; 544/116, 371; 546/148, 199; 548/362.5

[56] References Cited

U.S. PATENT DOCUMENTS

| | | | |
|---|---|---|---|
| 3,145,215 | 8/1964 | Kirchner | 540/603 |
| 5,552,398 | 9/1996 | King | 514/214 |

FOREIGN PATENT DOCUMENTS

| | | |
|---|---|---|
| 0347749 | 12/1989 | European Pat. Off. . |
| 410 509 | 1/1991 | European Pat. Off. . |
| 0491664 | 6/1991 | European Pat. Off. . |
| 358 903 | 3/1993 | European Pat. Off. . |
| 623 621 | 11/1994 | European Pat. Off. . |
| 93/03725 | 3/1993 | WIPO . |
| 93/24117 | 12/1993 | WIPO . |
| 94/00113 | 1/1994 | WIPO . |
| WO 94/07859 | 4/1994 | WIPO . |
| WO 94/27987 | 12/1994 | WIPO . |

OTHER PUBLICATIONS

Bockaert et al. "The 5ht4 receptor: a place in the sun" RIPS reviews, v. 13, pp. 141–145, 1992.
Taniyama et al. "Cisapride stimulates motility of the instetine via the 5HT receptors" Embase abst. No. 91337334, 1991.
Feletou et al. "Serotoninergic receptors subtype in coronary artery smooth muscle . . . " Medline Abst. 94133110, 1994.
Gidener et al. "Influence of serotnin on the human ureter . . . " Medline Abst. 96160103, 1996.
Miyashita et al. "A novel specific 5HT4 receptor . . . " Derwent Drug Abst. 92–33552, 1995.
Robert W. Hamilton, *J. Heterocyclic Chem.*, 13, 545–553.
Kaumann, et al., *Bio. Med. Chem. Let.*, 2, 419–420 (1992).
Derwent Abstract, Belgium 770068 (1970).
Derwent Abstract, Japanese 8081–858 (1972).

*Primary Examiner*—Ceila Chang
*Attorney, Agent, or Firm*—Robert D. Titus; David E. Boone

[57] ABSTRACT

Indazolecarboxamides are used as antagonists and partial agonists for the serotonin receptor 5-HT$_4$ and provide therapeutic methods for treatment of disorders caused by or affected by dysfunction of the 5-HT$_4$ receptor.

9 Claims, No Drawings

INDAZOLECARBOXAMIDES

CROSS REFERENCE

This application is a division, of application Ser. No. 08/485,956, filed on Jun. 7, 1995, U.S. Pat. No. 5,654,320 which application is a continuation-in-part of application Ser. No. 08/405,119, filed Mar. 16, 1995 abandoned.

FIELD OF THE INVENTION

The present invention belongs to the fields of pharmacology and synthetic organic chemistry, and provides a series of indazolecarboxamides which are partial agonists and antagonists of the serotonin 5-$HT_4$ receptor.

BACKGROUND OF THE INVENTION

Processes in the brain and other organs involving serotonin as a neurotransmitter have been a major field of pharmacological research for some decades. A large number of processes which depend on serotonin have been identified, and numerous therapeutic compounds which affect such processes are in widespread use. More than a dozen receptors which are acted upon by serotonin have been identified. Some of the receptors' physiological mechanisms have been identified, and others are still the subject of extended and active research.

One of the more recently identified serotonin receptors is known as 5-$HT_4$. Therapeutic methods making use of the 5-$HT_4$ receptor have been held back by the lack of compounds which affect the 5-$HT_4$ receptor without substantial effect at other receptors. The present invention provides a series of new pharmaceutical agents which have high affinity and selectivity at the 5-$HT_4$ receptor.

SUMMARY OF THE INVENTION

The present invention provides compounds of the formula

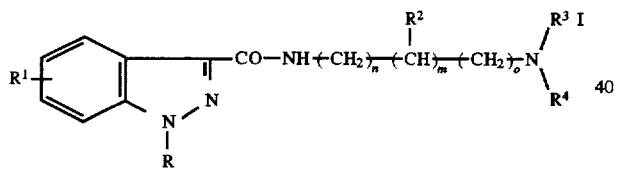

wherein:

R is hydrogen, $C_1$-$C_6$ alkyl, $C_3$-$C_6$ cycloalkyl;

$R^1$ is hydrogen, halo, $C_1$-$C_4$ alkyl, hydroxy, $C_1$-$C_4$ alkoxy or alkylthio, cyano, trifluoromethyl, carboxamido, mono- or di($C_1$-$C_4$ alkyl)carboxamido;

m, n and o are independently 0–5, provided that the sum of m, n and o is 2–5;

$R^2$ is hydrogen or $C_1$-$C_4$ alkyl;

$R^3$ and $R^4$ combine with the nitrogen atom to which they are attached to form 1-pyrrolidinyl, 1-piperazinyl, 1,2,3,4-tetrahydro-2-isoquinolinyl, 2,3-dihydro-1-indolinyl, 4-morpholinyl, 1-piperidinyl or 1-hexamethyleneiminyl, substituted with phenyl, naphthyl, (phenyl or naphthyl)($C_1$-$C_3$ alkyl), (phenyl or naphthyl)($C_1$-$C_3$ alkanoyl), amino, mono- or di($C_1$-$C_4$ alkyl)amino, or a group of the formula —NH—Y—$R^5$; provided that a piperazinyl or morpholinyl group may not be substituted with amino, mono- or di($C_1$-$C_4$ alkyl)amino, or —NH—Y—$R^5$;

wherein a phenyl or naphthyl group is unsubstituted or substituted with 1–3 halo, $C_1$-$C_3$ alkyl or $C_1$-$C_3$ alkoxy groups;

Y is carbonyl, sulfonyl, aminocarbonyl or oxycarbonyl;

$R^5$ is $C_1$-$C_6$ alkyl, $C_3$-$C_8$ cycloalkyl, $C_6$-$C_{11}$ bicyclo- or tricycloalkyl, (phenyl or naphthyl)($C_1$-$C_3$ alkyl), phenyl or naphthyl;

wherein a cycloalkyl, bicyclo- or tricycloalkyl, phenyl or naphthyl group is unsubstituted or substituted with 1–3 hydroxy, halo, $C_1$-$C_3$ alkyl or $C_1$-$C_3$ alkoxy groups;

or a pharmaceutically acceptable salt thereof.

The invention further provides pharmaceutical compositions comprising the above compounds and a pharmaceutically acceptable carrier, and provides pharmaceutical methods comprising the use of the compounds of Formula I, as well as of further compounds wherein the heterocyclic group formed by the combination of $R^3$ and $R^4$ with the nitrogen atom to which they are attached is unsubstituted.

The pharmaceutical methods of the present invention include a method of affecting the 5-$HT_4$ receptor, and in particular of providing partial agonist and antagonist activity at that receptor. Accordingly, the invention provides methods for the treatment or prophylaxis of disorders caused by or affected by dysfunction of the 5-$HT_4$ receptor. Such disorders for which the present compounds provide treatment or prophylaxis include pathologies of the central nervous system such as anxiety, pain, depression, schizophrenia, memory disorders, and dementia; pathologies of the gastrointestinal tract such as irritable bowel syndrome, nausea, gastroesophageal reflux disease, dyspepsia, gastrointestinal motility disorders, and constipation; cardiovascular disorders such as atrial fibrillation, arrhythmias and tachycardia; and genitourinary disorders such as urinary retention, urinary incontinence, and pain on urination.

The invention further provides a method of preparing those compounds of formula I wherein $R^3$ and $R^4$ combine with the nitrogen atom to which they are attached to form 1-pyrrolidinyl, 1,2,3,4-tetrahydro-2-isoquinolinyl, 2,3-dihydro-1-indolinyl, 1-piperidinyl or 1-hexamethyleneiminyl, substituted with a group of the formula —NH—Y—$R^5$;

Y is carbonyl;

$R^5$ is $C_3$-$C_8$ cycloalkyl, $C_6$-$C_{11}$ bicyclo- or tricycloalkyl, (phenyl or naphthyl)($C_1$-$C_3$ alkyl), phenyl or naphthyl;

wherein a cycloalkyl, bicyclo- or tricycloalkyl, phenyl or naphthyl group is substituted with 1–3 hydroxy groups;

or a pharmaceutically acceptable salt thereof; comprising reacting a compound of formula I wherein $R^3$ and $R^4$ combine with the nitrogen atom to which they are attached to form amino-substituted 1-pyrrolidinyl, 1,2,3,4-tetrahydro-2-isoquinolinyl, 2,3-dihydro-1-indolinyl, 1-piperidinyl or 1-hexamethyleneiminyl, with a compound of the formula

$HO_2C—R^5$ in the presence of a coupling agent for amide-forming reactions.

DESCRIPTION OF PREFERRED EMBODIMENTS

In the present document, all expressions of concentration, percent, ratio and the like will be expressed in weight units unless otherwise stated, except for mixtures of solvents which will be expressed in volume units. All temperatures not otherwise stated will be expressed in degrees Celsius.

Compounds

In the above general formula, the general chemical terms have their usual meanings. For example, the terms $C_1$–$C_6$ alkyl, $C_1$–$C_4$ alkyl and $C_1$–$C_3$ alkyl include groups such as methyl, ethyl, propyl, isobutyl, isopropyl, t-butyl, 2-ethylbutyl hexyl, isohexyl and the like. The terms $C_3$–$C_6$ cycloalkyl and $C_3$–$C_8$ cycloalkyl include groups such as cyclopropyl, cyclopentyl, cyclohexyl and cyclooctyl. The $C_1$–$C_4$ alkoxy, $C_1$–$C_4$ alkylthio and $C_1$–$C_3$ alkoxy groups include the corresponding alkyl groups linked through an oxygen atom or sulfur atom. The term $C_1$–$C_3$ alkanoyl includes carbonyl, acetyl and propionyl.

The term $C_6$–$C_{11}$ bicyclo- or tricycloalkyl includes groups such as bicyclo[2.2.0]hexyl, bicyclo[2.1.1]hexyl, bicyclo[3.2.0]heptyl, spiro[3.4]octyl, bicyclo[3.1.1]heptyl, bicyclo[4.2.0]octyl, spiro[3.5]nonyl, bicyclo[5.2.0]nonyl, bicyclo[7.2.0]undecyl, bicyclo[3.3.0]octyl, norbornyl, spiro[4.4]nonyl, bicyclo[4.3.0]nonyl, bicyclo[3.2.1]octyl, spiro[4.5]decyl, bicyclo[0.3.5]decyl, spiro[4.6]undecyl, adamantyl, tricyclo[1.3.3.0]nonyl, tricyclo[1.3.3.0]nonyl, tricyclo[3.3.0.0]octyl, and spiro[cyclopentyl-1.7']norbornyl.

The term halo includes chloro, fluoro, bromo and iodo.

The six-membered ring of the indazole group may be substituted at any of the four available positions with one of the $R^1$ groups, such as fluoro, ethyl, hydroxy, propoxy, methylthio, cyano, trifluoromethyl, carboxamido, N-ethylcarboxamido or N,N-dipropylcarboxamido.

The 1-position nitrogen atom of the indazole may be substituted with an R group, such as methyl, propyl or cyclopentyl.

The alkylene linking group

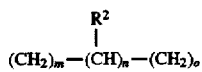

may be substituted with an alkyl $R^2$ group, such as methyl or isopropyl. It will be seen that the linking group comprises from 2 to 5 methylene groups, and that any of the methylene groups may be absent. Thus, the linking group may be substituted on each methylene, or may be unsubstituted, or may have an alkyl $R^2$ substituent at any position in the group. Thus, suitable linking groups include ethylene, propylene, pentylene, and the following groups:

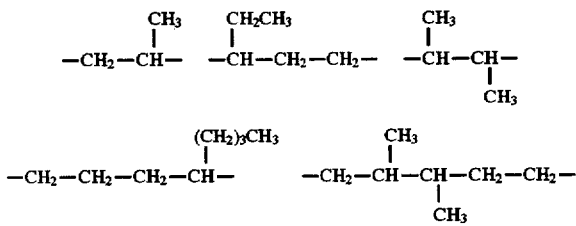

In the concept both of the novel compounds of the invention and the compounds for use in the treatment methods of the present invention, the groups $R^3$ and $R^4$ combine with the nitrogen atom to which they are attached to form a heterocyclic group. In the concept of the novel compounds of the present invention, the heterocyclic group thus formed is substituted, and in the concept of the compounds used in the present methods, the heterocyclic group may be unsubstituted or substituted.

Cyclic groups which are substituents on the heterocyclic group, or which are components of a substituent on the heterocyclic group, may be unsubstituted or substituted with one or more groups such as chloro, hydroxy, bromo, methyl, methoxy, ethyl, propoxy or isopropyl.

Since the heterocyclic groups formed by $R^3$ and $R^4$ can be somewhat complex in their substitution, a number of typical such groups will be illustrated below to assure full comprehension by the reader.

3-phenyl-1-piperidinyl
3-(4-chloro-6-ethyl-2-naphthyl)-1-piperazinyl
5-[2-(3-methylphenyl)ethyl]-1,2,3,4-tetrahydro-2-isoquinolinyl
5-(2,4,6-trichlorophenyl)acetyl-2,3-dihydro-1-indolinyl
3-(2-norbornylcarbonylamino)-1-pyrrolidinyl
3-(cyclooctylsulfonylamino)-1-piperidinyl
3-(hexylaminocarbonylamino)-1-hexamethyleneiminyl
4-[2-(4-chloro-3,5-dimethylphenyl)ethyl]oxycarbonylamino-1-piperidinyl
2-(4-bromo-3-ethoxy-1-naphthyl)carbonylamino-1-pyrrolidinyl
4-(6-fluoro-8-propyl-2-naphthyl)methylsulfonyl-amino-1-indolinyl
3-(1-adamantyl)oxycarbonylamino-1-pyrrolidinyl
6-(4-ethyl-2,6-difluorophenyl)aminocarbonylamino-2,3-dihydro-1-indolinyl
3-(3-phenylpropyl)carbonylamino-1-piperidinyl
3-(4-hydroxy-2-norbornylcarbonylamino)-1-pyrrolidinyl
3-(3-hydroxycycloheptylsulfonylamino)-1-piperidinyl
2-(4-hydroxy-2-fluoro-1-naphthyl)carbonylamino-1-pyrrolidinyl As described in formula I, the invention includes pharmaceutically acceptable salts of the compounds defined by the above formula. Compounds of this invention react with any of a number of nontoxic inorganic and organic acids to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

All of the compounds described in the present document are active and useful, but certain groups of the compounds are particularly interesting and are preferred. The following listing sets out several groups of preferred compounds. It will be understood that each of the listings may be combined with other listings to create additional, broader or more limited, groups of preferred compounds.

a) R is hydrogen.
b) R is $C_1$–$C_3$ alkyl or C5–C6 cycloalkyl.
c) R is hydrogen or $C_1$–$C_3$ alkyl.
d) R is hydrogen or secondary $C_1$–$C_6$ alkyl.

5 e) $R^1$ is hydrogen.

f) $R^1$ is hydrogen, halo, alkyl or alkoxy.

g) $R^2$ is hydrogen or methyl.

h) $R^2$ is hydrogen.

i) The sum of m, n and o is 2–4.

j) $R^3$ and $R^4$ combine with the nitrogen atom to which they are attached to form 1-pyrrolidinyl, 1-piperazinyl or 1-piperidinyl.

k) The substituent on the heterocyclic group formed by $R^3$, $R^4$ and the nitrogen atom is phenyl, naphthyl or (phenyl or naphthyl)($C_1$–$C_3$ $_{alkyl}$).

l) The substituent on the heterocyclic group formed by $R^3$, $R^4$ and the nitrogen atom is amino, or mono- or di($C_1$–$C_4$ alkyl)amino.

m) The substituent on the heterocyclic group formed by $R^3$, $R^4$ and the nitrogen atom is —NH—Y—$R^5$.

n) Y is carbonyl or sulfonyl.

o) Y is aminocarbonyl or oxycarbonyl.

p) $R^5$ is alkyl or cycloalkyl.

q) $R^5$ is adamantyl or norbornyl.

r) $R^5$ is phenyl, naphthyl or (phenyl or naphthyl)($C_1$–$C_3$ alkyl).

s) $R^5$ is substituted with 1–'hydroxy groups.

t) $R^5$ is adamantyl substituted with 1–3 hydroxy groups.

u) $R^5$ is cycloalkyl substituted with 1–3 hydroxy groups.

v) The compound is a pharmaceutically acceptable salt.

Synthesis

The compounds of the present invention are prepared from 1H-indazole-3-carboxylic acid, bearing the desired $R^1$ substituent, which are well-known compounds. The basic reaction in the synthesis is the formation of a carboxamide between the indazolecarboxylic acid and an amine compound made up of the linking group and the —N($R^3$)($R^4$) system. Formation of the amide is readily performed in a conventional manner, as with 1,1'-carbonyldiimidazole as an activating agent in any inert solvent at a moderate temperature. Tetrahydrofuran is usually a convenient and preferred solvent, in a process carried out at a temperature of about 0° to about 50°, usually preferably at ambient temperature.

Synthesis of the amine reactant is conventional, since the reactant is made up of conventionally used and readily reactive units. It will be understood that reactants having free amino groups, hydroxy groups and the like will need to be protected in the conventional manner during the reaction, and the protecting groups removed before isolation of the product.

Further, substituent groups on the heterocyclic combined $R^3$ and $R^4$ group frequently may conveniently be added as a second step, as by the reaction of such a heterocyclic group with, for example, an aroyl halide to provide a benzoyl or naphthylcarbonyl substituent, for example. Similarly, substituted sulfonyl halides may be used as the reactant to provide substituted sulfonamido substituents where Y is sulfonyl.

It is usually preferable to add the R substituent in a second step, after the rest of the molecule has been synthesized. Reaction with an iodine-substituted derivative of the desired R substituent, in the presence of a very strong base such as sodium hydride, readily provides the desired product. The reaction is best carried out at a cool temperature in the range from about 0° to about the ambient temperature; dimethylformamide is frequently a preferred solvent.

The particularly preferred process of this invention, illustrated in Examples 37 and 38 below, provides compounds of

6 formula I having hydroxy-substituted $R^5$ groups in an unexpectedly simple manner. An artisan would expect that the hydroxy group of the starting compound must be protected to prevent the formation of undesired polymeric substances. The examples below demonstrate, however, that reaction with the unprotected hydroxy compounds proceeds smoothly in excellent yield and purity. The process may be carried out at temperatures from about 0° C. to 80° C., preferably ambient temperature to about 60° C., in protic solvents such as halogenated alkanes such as methylene chloride, chloroform and ethylene dichloride, amides such as dimethylformamide and dimethylacetamide, and ethers such as diethyl ether and tetrahydrofuran. No special protection from moisture or oxygen is necessary. The preferred coupling agent is carbonyldiimidazole, but any coupling agent such as are commonly used to assist in forming amide bonds, especially in peptide chemistry is useful. See, e.g., *The Peptides*, Gross and Meienhofer, Eds., Academic Press (1979), Ch. 2, for such coupling agents.

Further information about the synthesis of the present compounds may be obtained from the following preparative examples. The skilled reader will understand that the examples are illustrative but not exhaustive, and numerous useful variations of the process will occur to the reader.

EXAMPLE 1

Preparation of N-[2-(1-piperidinyl)ethyl]-1H-indazole-3-carboxamide hydrochloride To a solution of 1H-indazole-3-carboxylic acid (0.778 g, 4.8 mmol) in 25 mL tetrahydrofuran, was added 1,1'-carbonyl-diimidazole (0.778 g, 4.8 mmol). This solution was stirred at room temperature for 3 h. To it was added dropwise a solution of 1-(2-aminoethyl)piperidine (0.615 g, 4.8 mmol) dissolved in 3.0 mL tetrahydrofuran. This solution was then stirred at room temperature for 18 h, and was evaporated and diluted with water. Extraction with ethyl acetate followed by water and brine washes gave 1.14 g of low melting solid. Crystallization as the hydrochloride salt from ethyl acetate/methanol provided 0.407 g of colorless crystals. Mp 252° C. Mass spectrum, $m^+$=273. Anal ($C_{15}H_{21}ClN_4O$) theory C, 58.34; H, 6.85; N, 18.14; found C, 58.57; H, 6.97; N, 18.02.

EXAMPLE 2

Preparation of N-[2-(1-piperidinyl)ethyl]-1-(2-propyl)-1H-indazole-3-carboxamide hydrochloride A portion of the free base of Example 1 (1.41 g, 5.17 mmol) was stirred in 35 mL dimethylformamide at room temperature while sodium hydride (0.207 g, 5.17 mmol, as a 60% mineral oil dispersion) was added. After stirring at room temperature for 4 h, the reaction mixture was cooled in an ice bath to 15° C. and 2-iodopropane (0.57 mL, 5.7 mmol) was added dropwise. The resulting mixture was stirred at room temperature for 18 h, and the solvent was evaporated and the residue was dissolved in ethyl acetate. After washing the ethyl acetate solution with a 10% sodium carbonate solution, water and brine, evaporation afforded 1.76 g of oil. Flash chromatography [silica gel, methylene chloride/methanol (85/15)] yielded 1.35 g oil. Crystallization as the hydrochloride salt from ethyl acetate/methanol provided 1.109 g of colorless crystals. Mp>250° C. Mass spectrum, $m^+$=314. Anal ($C_{18}H_{27}ClN_4O$) theory C, 61.61; H, 7.76; N, 15.97; found C, 61.85; H, 7.79; N, 15.98.

EXAMPLE 3

Preparation of N-[3-(1-piperidinyl)propyl]-1H-indazole-3-carboxamide

Same procedure followed as described in Example 1. The following amounts were used: 1H-indazole-3-carboxylic acid (0.65 g, 4 mmol), 1,1'-carbonyldiimidazole (0.65 g, 4 mmol) and 1-(3-aminopropyl)piperidine (0.57 g, 4 mmol). The ethyl acetate extracts were evaporated to 0.906 g oil. Flash chromatography [silica gel, methylene chloride/ methanol/ammonium hydroxide (100/10/0.5)] yielded 0.457 g oil. Mass spectrum, $m^+=287$.

EXAMPLE 4

Preparation of N-[3-(1-piperidinyl)propyl]-1-(2-propyl)-1H-indazole-3-carboxamide hydrochloride Same procedure followed as described in Example 2. The following amounts were used: Product from Example 3 (0.457 g, 1.6 mmol), sodium hydride (0.064 g, 1.6 mmol, as a 60% mineral oil dispersion) and 2-iodopropane (0.18 mL, 1.76 mmol). Flash chromatography [silica gel, methylene chloride/methanol/ ammonium hydroxide (100/2.5/0.5)] yielded 0.366 g oil. Crystallization as the hydrochloride salt from ethyl acetate/methanol provided 0.145 g of colorless crystals. Mp 156°–158° C. Mass spectrum, $m^+=329$. Anal ($C_{19}H_{29}ClN_4O$) theory C, 62.54; H, 8.01; N, 15.35; found C, 62.69; H, 7.91; N, 15.60.

EXAMPLE 5

Preparation of N-[4-(1-piperidinyl)butyl]-1H-indazole-3-carboxamide

To a solution of 1H-indazole-3-carboxylic acid (0.745 g, 4.6 mmol) in 20 mL dimethylformamide, was added 1,1'-carbonyldiimidazole (0.745 g, 4.6 mmol). This mixture was stirred at room temperature for 4 h, and to it was added dropwise a solution of 1-(4-aminobutyl)piperidine (0.718 g, 4.6 mmol) dissolved in 3 mL dimethylformamide. This solution was then stirred at room temperature for 18 h, the volatiles were evaporated and the residue was diluted with water. Extraction with ethyl acetate followed by water and brine washes gave 1.40 g of an oil which was sufficiently pure for use in the next reaction. Mass spectrum, $m^+=301$.

EXAMPLE 6

Preparation of N-[4-(1-piperidinyl)butyl]-1-(2-propyl)-1H-indazole-3-carboxamide oxalate Same procedure followed as described in Example 2. The following amounts were used: Product from Example 5 (1.40 g, 4.66 mmol), sodium hydride (0.190 g, 4.66 mmol, as a 60% mineral oil dispersion) and 2-iodopropane (0.52 mL, 5.13 mmol). The ethyl acetate extracts yielded 1.48 g oil. Two crystallizations as the oxalate salt from 2-propanol provided 0.41 g of colorless crystals. Mp 143° C. Mass spectrum, $m^+=343$. Anal ($C_{22}H_{32}N_4O_5$) theory C, 61.09; H, 7.46; N, 12.95; found C, 61.05; H, 7.51; N, 13.02.

Preparation 1

Preparation of 1-(2-aminoethyl)-4-benzyloxycarbonylaminopiperidine

To a cold (10° C.) stirred mixture of 4-amino-1-benzyl-piperidine (15.2 g, 80 mmol), sodium bicarbonate (9.54 g, 110 mmol), 310 mL tetrahydrofuran and 155 mL water, was added dropwise benzyl chloroformate (14.0 mL, 98 mmol). The resulting mixture was stirred at 5°–10° C. for 2 h. The reaction mixture was poured onto 1000 mL water. Extraction with ethyl acetate, washing with brine, drying and evaporation of the ethyl acetate gave a viscous oil. Trituration with hexanes provided 18.56 g of solid. Mp 74°–76° C. Mass spectrum, $m^+=324$.

The intermediate above (18.5 g, 57 mmol) was stirred in 300 mL of 1,2-dichloroethane and cooled in an ice bath to 5° C., while 1-chloroethyl chloroformate (12.3 mL, 114 mmol) was added dropwise. After stirring at room temperature for 1 h, the 1,2-dichloroethane was evaporated to a residue. 300 mL of methanol was added to the residue and the solution heated at reflux temperature for 1 h. Evaporation of the methanol, addition of 300 mL ethyl acetate and filtration provided 15.67 g of yellow solid. Mp 178° C. Mass spectrum, $m^+=235$.

The intermediate above (2.07 g, 7.6 mmol), N-(2-bromoethyl)phthalimide (1.94 g, 7.6 mmol) and sodium carbonate (2.83 g, 26.6 mmol) were heated together in 40 mL dimethylformamide at 100° C. for 18 h. Evaporation of the dimethylformamide, dilution with water and extraction with ethyl acetate followed by water washing, brine washing and drying provided, after evaporation, 3.15 g of solid. Crystallization from ethanol provided 1.58 g colorless crystals. Mp 159°–161° C. Mass spectrum, $m^+=407$. Anal ($C_{23}H_{25}N_3O_4$) theory C, 57.80; H, 6.18; N, 10.31; found C, 57.71; H, 6.32; N, 10.20.

The intermediate prepared as above (11.9 g, 29.2 mmol) was stirred in 600 mL ethanol while 15.8 mL of hydrazine hydrate was added. This mixture was heated at reflux temperature for 4 h. After cooling, the precipitate was filtered and the filtrate was evaporated to a residue. To this residue was carefully added 250 mL of 1N sodium hydroxide solution, followed by addition of solid sodium chloride until the solution was saturated. Repeated extraction with diethyl ether, drying and evaporation gave 8.19 g of oil. Mass spectrum, $m^+=278$.

EXAMPLE 7

Preparation of N-[2-(4-benzyloxycarbonylamino-1-piperidinyl)ethyl]-1H-indazole-3-carboxamide Same procedure followed as described in Example 5. The following amounts were used: 1H-indazole-3-carboxylic acid (4.70 g, 29 mmol), 1,1'-carbonyldiimidazole (4.70 g, 29 mmol) and the intermediate from Preparation 1 (8.10 g, 29 mmol). The ethyl acetate extracts were evaporated to give 11.17 g of a solid which was sufficiently pure for use in the next reaction. Mp 184°–187° C. Mass spectrum, $m^+=422$.

EXAMPLE 8

Preparation of N-[2-(4-benzyloxycarbonylamino-1-piperidinyl)ethyl]-1-(2-propyl)-1H-indazole-3-carboxamide oxalate Same procedure followed as described in Example 2. The following amounts were used: Product from Example 7 (11.1 g, 26.3 mmol), sodium hydride (1.05g, 26.3 mmol, as a 60% mineral oil dispersion) and 2-iodopropane (2.90 mL, 29 mmol). Flash chromatography [silica gel, methylene chloride/methanol (95/5)] yielded 10.60 g oil. Crystallization as the oxalate salt from ethyl acetate/methanol provided colorless crystals. Mp 149°–151° C. Mass spectrum, $m^+=463$. Anal ($C_{28}H_{35}N_5O_7$) theory C, 60.75; H, 6.37; N, 12.65; found C, 60.53; H, 6.37; N, 12.47.

EXAMPLE 9

Preparation of N-[2-(1-pyrrolidinyl)ethyl]-1H-indazole-3-carboxamide

Same procedure followed as described in Example 1. The following amounts were used: 1H-indazole-3-carboxylic acid (0.65 g, 4 mmol), 1,1'-carbonyldiimidazole (0.65 g, 4 mmol) and 1-(2-aminoethyl)pyrrolidine (0.458 g, 4 mmol). The ethyl acetate extracts were evaporated to 0.754 g oil. Flash chromatography |silica gel, methylene chloride/methanol/ammonium hydroxide (100/10/0.5)| yielded 0.421 g oil. Mass spectrum, $m^+=258$.

EXAMPLE 10

Preparation of N-[2-(1-pyrrolidinyl)ethyl]-1-(2-propyl)-1H-indazole-3-carboxamide hydrochloride Same procedure followed as described in Example 2. The following amounts were used: Product from Example 9 (0.421 g, 1.63 mmol), sodium hydride (0.065 g, 1.63 mmol, as a 60% mineral oil dispersion) and 2-iodopropane (0.18 mL, 1.77 mmol). The ethyl acetate extracts were evaporated to 0.526 g oil. Flash chromatography |silica gel, methylene chloride/methanol/ammonium hydroxide (100/5/0.5)| yielded 0.385 g oil. Crystallization as the hydrochloride salt from ethyl acetate/methanol provided 0.197 g colorless crystals. Mp 210°–212° C. Mass spectrum, $m^+=300$. Anal ($C_{17}H_{25}ClN_4O$) theory C, 60.61; H, 7.48; N, 16.63; found C, 60.44; H, 7.21; N, 16.58.

Preparation 2

Preparation of N-(2-aminoethyl) hexamethyleneimine

Hexamethyleneimine (5.7 mL, 50 mmol), N-(2-bromoethyl)phthalimide (12.7 g, 50 mmol) and sodium carbonate (13.3 g, 125 mmol) were heated together in 250 mL dimethylformamide at 100° C. for 18 h. Evaporation of the dimethylformamide, dilution with water and extraction with ethyl acetate followed by water washing, brine washing and drying provided, after evaporation, 12.71 g oil. Crystallization as the tosylate salt from 2-propanol provided 13.29 g colorless crystals. Mp 180°–182° C. Mass spectrum, $m^+=272$. Anal ($C_{23}H_{28}N_2O_5S$) theory C, 62.14; H, 6.35; N, 6.30; found C, 62.37; H, 6.19; N, 6.35.

The intermediate above (as the free base) (3.33 g, 12.2 mmol) was stirred in 220 mL ethanol while 5.0 mL of hydrazine hydrate was added. This mixture was heated at reflux temperature for 4 h. After cooling, the mixture was filtered and the filtrate was evaporated to a residue. This residue was carefully diluted with a 1N sodium hydroxide solution, followed by extraction with diethyl ether, drying and evaporation to give 1.33 g of oil. This material was suitable for use in the next reaction.

EXAMPLE 11

Preparation of N-[2-(1-hexamethyleneiminyl)ethyl]-1H-indazole-3-carboxamide

Same procedure followed as described in Example 5. The following amounts were used: Intermediate from Preparation 2 (1.33 g, 9.3 mmol), 1H-indazole-3-carboxylic acid (1.51 g, 9.3 mmol) and 1,1'-carbonyldiimidazole (1.51 g, 9.3 mmol). The ethyl acetate extracts were evaporated to a solid. Addition of cyclohexane and filtration provided 2.46 g of solid. Mp 104°–115° C. Mass spectrum, $m^+=287$.

EXAMPLE 12

Preparation of N-[2-(1-hexamethyleneiminyl)ethyl]-1-(2-propyl)-1H-indazole-3-carboxamide hydrochloride Same procedure followed as described in Example 2. The following amounts were used: Product from Example 11 (2.45 g, 8.55 mmol), sodium hydride (0.342 g, 8.55 mmol, as a 60% mineral oil dispersion) and 2-iodopropane (0.94 mL, 9.4 mmol). The ethyl acetate extracts were evaporated to 3.0 g oil. Flash chromatography |silica gel, methylene chloride/methanol (85/15)| yielded 1.39 g oil. Crystallization as the hydrochloride salt from ethyl acetate/methanol provided 1.05 g colorless crystals. Mp 216°–218° C. Mass spectrum, $m^+=328$. Anal ($C_{19}H_{29}ClN_4O$) theory C, 62.54; H, 8.01; N, 15.35; found C, 62.52; H, 8.09; N, 15.48.

EXAMPLE 13

Preparation of N-[2-(4-morpholinyl)ethyl]-1H-indazole-3-carboxamide

Same procedure followed as described in Example 1. The following amounts were used: 1H-indazole-3-carboxylic acid (0.65 g, 4 mmol), 1,1'-carbonyldiimidazole (0.65 g, 4 mmol) and 4-(2-aminoethyl)morpholine (0.52 mL, 4 mmol). The ethyl acetate extracts were evaporated to 0.468 g solid. Crystallization from ethyl acetate provided 0.267 g colorless crystals. Mass spectrum, $m^+=274$.

EXAMPLE 14

Preparation of N-[2-(4-morpholinyl)ethyl]-1-(2-propyl)-1H-indazole-3-carboxamide hydrochloride Same procedure followed as described in Example 2. The following amounts were used: Product from Example 13 (0.267 g, 0.97 mmol), sodium hydride (0.040 g, 0.97 mmol, as a 60% mineral oil dispersion) and 2-iodopropane (0.107 mL, 1.07 mmol). The ethyl acetate extracts were evaporated to 0.324 g oil. Two crystallizations as the hydrochloride salt from ethyl acetate/methanol provided 0.122 g colorless crystals. Mp 201°–203° C. Mass spectrum, $m^{30}=316$. Anal ($C_{17}H_{25}ClN_4O_2$) theory C, 57.87; H, 7.14; N, 15.88; found C, 57.71; H, 7.04; N, 16.07.

Preparation 3

Preparation of 1-(2-aminoethyl)-4-benzylpiperazine

1-Benzylpiperazine (8.81 g, 50 mmol), N-(2-bromoethyl) phthalimide (12.7 g, 50 mmol) and sodium carbonate (13.25 g, 125 mmol) were heated together in 250 mL dimethylformamide at 100° C. for 18 h. Evaporation of the dimethylformamide, dilution with water and extraction with ethyl acetate followed by water washing, brine washing and drying, provided, after evaporation, 18.47 g oil. Crystallization as the dihydrochloride salt from methanol provided 8.70 g colorless crystals. Mp>250° C. Mass spectrum, $m^+=349$. Anal ($C_{21}H_{25}Cl_2N_3O_2$) theory C, 59.72; H, 5.97; N, 9.95; found C, 60.04; H, 6.00; N, 10.04.

The intermediate above (8.48 g, 20 mmol) was stirred in 400 mL ethanol while 10.0 mL of hydrazine hydrate was added. This mixture was heated at reflux temperature for 4 h. After cooling, the mixture was filtered and the filtrate was evaporated to a residue. This residue was carefully diluted with 300 mL 1N sodium hydroxide solution, followed by extraction with diethyl ether, drying and evaporation to give 3.69 g of oil. Mass spectrum, $m^+=219$.

EXAMPLE 15

Preparation of N-[2-(4-benzyl-1-piperazinyl)ethyl]-1H-indazole-3-carboxamide

Same procedure followed as described in Example 5. The following amounts were used: 1H-indazole-3-carboxylic acid (2.72 g, 16.7 mmol), 1,1'-carbonyldiimidazole (2.72 g, 16.7 mmol) and the intermediate from Preparation 3 (3.68 g, 16.7 mmol). The ethyl acetate extracts were evaporated to 5.72 g solid. Mass spectrum, m⁺=364.

EXAMPLE 16

Preparation of N-[2-(4-benzyl-1-piperazinyl)ethyl]-1-(2-propyl)-1H-indazole-3-carboxamide dihydrochloride Same procedure followed as described in Example 2. The following amounts were used: Product from Example 15 (5.72 g, 15.7 mmol), sodium hydride (0.630 g, 15.7 mmol, as a 60% mineral oil dispersion) and 2-iodopropane (1.73 mL, 17.3 mmol). The ethyl acetate extracts were evaporated to 7.24 g oil. Flash chromatography [silica gel, methylene chloride/methanol (93/7)] yielded 2.85 g oil. Crystallization as the dihydrochloride salt from 2-propanol provided colorless crystals. Mp 242° C. Mass spectrum, m⁺=405. Anal ($C_{24}H_{33}Cl_2N_5O$) theory C, 60.25; H, 6.95; N, 14.64; found C, 60.04; H, 7.01; N, 14.53.

EXAMPLE 17

Preparation of N-[2-(1-piperazinyl)ethyl]-1-(2-propyl)-1H-indazole-3-carboxamide The product from Example 16, as the free base (2.35 g, 5.8 mmol), was reacted with hydrogen gas in the presence of 5% Pd/C (40° C./18 h/60 PSI) in an ethanol solution. After filtering the catalyst, the ethanol was evaporated to 1.49 g oil. Flash chromatography [silica gel, methylene chloride/methanol/ammonium hydroxide (100/15/0.5)] yielded 0.951 g oil. Mass spectrum, m⁺=315.

EXAMPLE 18

Preparation of N-[2-(4-benzoyl-1-piperazinyl)ethyl]-1-(2-propyl)-1H-indazole-3-carboxamide oxalate The product from Example 17 (0.315 g, 1 mmol) and triethylamine (0.146 mL, 1.05 mmol) were stirred in 10.0 mL tetrahydrofuran and cooled briefly in an ice bath. To the mixture was added dropwise benzoyl chloride (0.116 mL, 1 mmol) and the resulting mixture was stirred 18 h at room temperature, filtered and evaporated to an oil. Crystallization as the oxalate salt from ethyl acetate/methanol provided 0.284 g colorless crystals. Mp 105° C. Mass spectrum, m⁺=419. Exact mass theory, 419.2321; found, 419.2315.

Preparation 4

Preparation of 1-(2-aminoethyl)-4-benzylpiperidine

4-Benzylpiperidine (5.30 mL, 30 mmol), N-(2-bromoethyl)phthalimide (7.6 g, 30 mmol) and sodium carbonate (7.95 g, 75 mmol) were heated together in 150 mL dimethylformamide at 100° C. for 18 h. Evaporation of the dimethylformamide, dilution with water and extraction with ethyl acetate followed by water washing, brine washing and drying, provided, after evaporation, 11.61 g oil. Crystallization as the tosylate salt from ethanol provided 10.39 g colorless crystals. Mp 194°–196° 1 C. Mass spectrum, m⁺=348. Anal ($C_{29}H_{32}N_2 O_5S$) theory C, 66.90; H, 6.20; N, 5.38; found C, 66.68; H, 6.40; N, 5.16.

The intermediate above as the free base (5.05 g, 14 mmol) was stirred in 225 mL ethanol while 5.0 mL of hydrazine hydrate was added. This mixture was heated at reflux temperature for 4 h. After cooling, the mixture was filtered and the filtrate was evaporated to a residue. This residue was carefully diluted with a 1N sodium hydroxide solution, followed by extractions with diethyl ether, drying and evaporation to give 3.13 g of oil. Mass spectrum, m⁺=218.

EXAMPLE 19

Preparation of N-[2-(4-benzyl-1-piperidinyl)ethyl]-1H-indazole-3-carboxamide

Same procedure followed as described in Example 5. The following reactants and amounts were used: 1H-indazole-3-carboxylic acid (1.62 g, 10 mmol), 1,1'-carbonyldiimidazole (1.62 g,10 mmol) and the intermediate from Preparation 4 (2.18 g, 10 mmol). The ethyl acetate extracts were evaporated to a solid. Addition of cyclohexane and filtration provided 3.52 g of solid. Mass spectrum, m⁺=363.

EXAMPLE 20

Preparation of N-[2-(4-benzyl-1-piperidinyl)ethyl]-1-(2-propyl)-1H-indazole-3-carboxamide oxalate Same procedure followed as described in Example 2. The following amounts were used: Product from Example 19 (3.50 g, 9.7 mmol), sodium hydride (0.390 g, 9.7 mmol, as a 60% mineral oil dispersion) and 2-iodopropane (1.07 mL, 10.7 mmol). The ethyl acetate extracts were evaporated to 4.30 g oil. Flash chromatography [silica gel, methylene chloride/methanol (93/7)] yielded 2.52 g oil. Crystallization as the oxalate salt from ethanol provided 2.51 g of colorless crystals. Mp 149° C. Mass spectrum, m⁺=404. Anal ($C_{27}H_{34}N_4O_5$) theory C, 65.57; H, 6.93; N, 11.33; found C, 65.32; H, 6.86; N, 11.48.

Preparation 5

Preparation of 2-(2-aminoethyl)-1,2,3,4-tetrahydroisoquinoline 1,2,3,4-Tetrahydroisoquinoline (3.76 mL, 30 mmol), N-(2-bromoethyl)phthalimide (7.6 g, 30 mmol) and sodium carbonate (8.0 g, 75 mmol) were heated together in 150 mL dimethylformamide at 100° C. for 18 h. Evaporation of the dimethylformamide, dilution with water and extraction with ethyl acetate followed by water washing, brine washing and drying, provided, after evaporation, 10.46 g oil. Crystallization as the tosylate salt from ethanol provided 10.30 g colorless crystals. Mp 196°–198° C. Mass spectrum, m⁺=306. Anal ($C_{26}H_{26}N_2O_5S$) theory C, 65.26; H, 5.48; N, 5.85; found C, 65.37; H, 5.45; N, 5.95.

The intermediate above as the free base (3.06 g, 10 mmol) was stirred in 200 mL ethanol while 5.0 mL of hydrazine hydrate was added. This mixture was heated at reflux temperature for 4 h. After cooling, the mixture was filtered and the filtrate was evaporated to a residue. This residue was carefully diluted with a 1N sodium hydroxide solution, followed by extraction with diethyl ether, drying and evaporation to give 1.62 g of oil. Mass spectrum, m⁺=176.

EXAMPLE 21

Preparation of N-[2-(1,2,3,4-tetrahydro-2-isoquinolinyl)ethyl]-1H-indazole-3-carboxamide Same procedure followed as described in Example 5. The following amounts were used: 1H-indazole-3-carboxylic acid (1.49 g, 9.2 mmol), 1,1'-carbonyldiimidazole (1.49 g, 9.2 mmol) and the intermediate from Preparation 5 (1.62 g, 9.2 mmol). The ethyl acetate extracts were evaporated to a solid. Addition of cyclohexane and filtration provided 2.73 g of solid. Mass spectrum, $m^+$=321.

EXAMPLE 22

Preparation of N-[2-(1,2,3,4-tetrahydro-2-isoquinolinyl)ethyl]-1-(2-propyl)-1H-indazole-3-carboxamide oxalate Same procedure followed as described in Example 2. The following amounts were used: Product from Example 21 (2.70 g, 8.5 mmol), sodium hydride (0.340 g, 8.5 mmol, as a 60% mineral oil dispersion) and 2-iodopropane (0.94 mL, 9.4 mmol). The ethyl acetate extracts were evaporated to 3.28 g oil. Flash chromatography [silica gel, methylene chloride/methanol (97/3)] yielded 2.62 g oil. Crystallization as the oxalate salt from ethanol provided 2.47 g of colorless crystals. Mp 191° C. Mass spectrum, $m^+$=362. Anal ($C_{24}H_{28}N_4O_5$) theory C, 63.70; H, 6.24; N, 12.38; found C, 63.96; H, 6.47; N, 12.26.

EXAMPLE 23

Preparation of N-[2-(4-amino-1-piperidinyl)ethyl]-1-(2-propyl)-1H-indazole-3-carboxamide dioxalate The product from Example 8, as the free base (8.71 g, 18.8 mmol), was reacted with hydrogen gas in the presence of 5% Pd/C (25° C./18 h/60 PSI) in an ethanol solution. After filtering the catalyst, the ethanol was evaporated to 5.0 g oil. Crystallization as the dioxalate salt from methanol/water provided colorless crystals. Mp 232° C. Mass spectrum, $m^+$=329. Anal ($C_{22}H_{31}N_5O_9$) theory C, 51.86; H, 6.13; N, 13.75; found C, 51.61; H, 6.04; N, 13.48.

EXAMPLE 24

Preparation of N-[2-(4-methylsulfonylamino-1-piperidinyl)ethyl]-1-(2-propyl)-1H-indazole-3-carboxamide oxalate The product from Example 23, as the free base (0.330 g, 1 mmol) and triethylamine (0.15 mL, 1.05 mmol) were stirred in 10.0 mL tetrahydrofuran and cooled briefly in an ice bath. To the mixture was added dropwise methanesulfonyl chloride (0.08 mL, 1 mmol) and the resulting mixture was stirred 18 h at room temperature. The mixture was filtered and the filtrate was evaporated to 0.401 g oil. Flash chromatography [silica gel, methylene chloride/methanol (90/10)] yielded 0.147 g oil. Crystallization as the oxalate salt from ethyl acetate/methanol provided 0.149 g colorless crystals. Mp 204° C. Mass spectrum, $m^+$=407. Exact mass theory, 408.2069; found, 408.2066.

EXAMPLE 25

Preparation of N-[2-(4-benzoylamino-1-piperidinyl)ethyl]-1-(2-propyl)-1H-indazole-3-carboxamide oxalate The product from Example 23, as the free base (0.330 g, 1 mmol) and triethylamine (0.15 mL, 1.05 mmol) were stirred in 10.0 mL tetrahydrofuran and cooled briefly in an ice bath. To the mixture was added dropwise benzoyl chloride (0.116 mL, 1 mmol) and the resulting mixture was stirred 18 h at room temperature and filtered and the filtrate was evaporated to 0.498 g oil. Crystallization as the oxalate salt from ethyl acetate/methanol provided 0.265 g colorless crystals. Mp 130° C. Mass spectrum, $m^+$=433. Anal ($C_{27}H_{33}N_5O_6$) theory C, 61.94; H, 6.35; N, 13.38; found C, 61.73; H, 6.35; N, 13.33.

EXAMPLE 26

Preparation of N-[2-(4-benzylcarbonylamino-1-piperidinyl)-ethyl]-1-(2-propyl)-1H-indazole-3-carboxamide oxalate The product from Example 23, as the free base (0.310 g, 0.94 mmol) and triethylamine (0.13 mL, 0.94 mmol) were stirred in 10.0 mL tetrahydrofuran and cooled briefly in an ice bath. To the mixture was added dropwise phenylacetyl chloride (0.12 mL, 0.94 mmol) and the resulting mixture was stirred 18 h at room temperature and filtered, and the filtrate was evaporated to an oil. Crystallization as the oxalate salt from ethyl acetate/methanol provided 0.176 g colorless crystals. Mp 168° C. Mass spectrum, $m^+$=447. Anal ($C_{28}H_{35}N_5O_6$) theory C, 62.56; H, 6.56; N, 13.03; found C, 62.61; H, 6.65; N, 12.83.

EXAMPLE 27

Preparation of N-[2-(4-(1-adamantylcarbonylamino)-1-piperidinyl)ethyl]-1-(2-propyl)-1H-indazole-3-carboxamide oxalate The product from Example 23, as the free base (0.330 g, 1 mmol) and triethylamine (0.15 mL, 1.05 mmol) were stirred in 10.0 mL tetrahydrofuran and cooled briefly in an ice bath. To the mixture was added, in portions, 1-adamantanecarbonyl chloride (0.199 g, 1 mmol) and the resulting mixture was stirred 18 h at room temperature and filtered, and the filtrate was evaporated to 0.565 g oil. Crystallization as the oxalate salt from ethyl acetate/methanol provided 0.267 g colorless crystals. Mp 228° C. Mass spectrum, $m^+$=491. Anal ($C_{31}H_{43}N_5O_6$) theory C, 64.01; H, 7.45; N, 12.04; found C, 63.89; H, 7.53; N, 12.12.

EXAMPLE 28

Preparation of N-[2-(4-acetylamino-1-piperidinyl)ethyl]-1-(2-propyl)-1H-indazole-3-carboxamide oxalate The product from Example 23, as the free base (0.330 g, 1 mmol) and triethylamine (0.15 mL, 1.05 mmol) were stirred in 10.0 mL tetrahydrofuran and cooled briefly in an ice bath. To the mixture was added dropwise acetyl chloride (0.071 mL, 1 mmol) and the resulting mixture was stirred 18 h at room temperature and filtered, and the filtrate was evaporated to 0.360 g oil. Crystallization as the oxalate salt from ethyl acetate/methanol provided 0.243 g colorless crystals. Mp 176° C. Mass spectrum, $m^+$=371. Anal ($C_{22}H_{31}N_5O_6$) theory C, 57.25; H, 6.77; N, 15.17; found C, 56.95; H, 6.74; N, 14.99.

EXAMPLE 29

Preparation of N-[2-(4-propionylamino-1-piperidinyl)ethyl]-1-(2-propyl)-1H-indazole-3-carboxamide oxalate The product from Example 23, as the free base (0.310 g, 0.94 mmol) and triethylamine (0.13 mL, 0.94 mmol) were stirred in 10.0 mL tetrahydrofuran and cooled briefly in an ice bath. To the mixture was added dropwise propionyl chloride (0.08 mL, 0.94 mmol) and the resulting mixture was stirred 18 h at room temperature and filtered, and the filtrate was evaporated to an oil. Crystallization as the oxalate salt from ethyl acetate/methanol provided 0.168 g colorless crystals. Mp 169° C. Mass spectrum. m$^+$=385. Anal ($C_{23}H_{33}N_5O_6$) theory C, 58.09; H, 6.99; N, 14.73; found C, 57.79; H, 6.93; N, 14.46.

EXAMPLE 30

Preparation of N-[2-(4-butyrylamino-1-piperidinyl) ethyl]-1-(2-propyl)-1H-indazole-3-carboxamide oxalate The product from Example 23, as the free base (0.330 g, 1 mmol) and triethylamine (0.15 mL, 1.05 mmol) were stirred in 10.0 mL tetrahydrofuran and cooled briefly in an ice bath. To the mixture was added dropwise butyryl chloride (0.1 mL, 1 mmol) and the resulting mixture was stirred 18 h at room temperature and filtered, and the filtrate was evaporated to 0.389 g oil. Crystallization as the oxalate salt from ethyl acetate/methanol provided 0.149 g colorless crystals. Mp 122° C. Mass spectrum. m$^+$=399. Anal ($C_{24}H_{35}N_5O_6$) theory C, 58.88; H, 7.21; N, 14.32; found C, 58.60; H, 7.15; N, 14.30.

EXAMPLE 31

Preparation of N-[2-(4-valerylamino-1-piperidinyl) ethyl]-1-(2-propyl)-1H-indazole-3-carboxamide The product from Example 23, as the free base (0.330 g, 1 mmol) and triethylamine (0.15 mL, 1.05 mmol) were stirred in 10.0 mL tetrahydrofuran and cooled briefly in an ice bath. To the mixture was added dropwise valeryl chloride (0.12 mL, 1 mmol) and the resulting mixture was stirred 18 h at room temperature and filtered, and the filtrate was evaporated to 0.385 g oil. Crystallization from diethyl ether provided 0.176 g colorless crystals. Mp 107°–109° C. Mass spectrum, m$^+$=413. Anal ($C_{23}H_{35}N_5O_2$) theory C, 66.80; H, 8.53; N, 16.93; found C, 66.59; H, 8.66; N, 17.04.

EXAMPLE 32

Preparation of N-[2-(4-isobutyrylamino-1-piperidinyl)ethyl]-1-(2-propyl)-1H-indazole-3-carboxamide oxalate The product from Example 23, as the free base (0.330 g, 1 mmol) and triethylamine (0.15 mL, 1.05 mmol) were stirred in 10.0 mL tetrahydrofuran and cooled briefly in an ice bath. To the mixture was added dropwise isobutyryl chloride (0.10 mL, 1 mmol) and the resulting mixture was stirred 18 h at room temperature and filtered, and the filtrate was evaporated to 0.417 g oil. Crystallization as the oxalate salt from 2-propanol provided 0.194 g colorless crystals. Mp 193° C. Mass spectrum, m$^+$=399. Anal ($C_{24}H_{35}N_5O_6$) theory C, 58.88; H, 7.21; N, 14.30; found C, 58.60; H, 6.95; N, 14.11.

EXAMPLE 33

Preparation of N-[2-(4-trimethylacetylamino-1-piperidinyl)-ethyl]-1-(2-propyl)-1H-indazole-3-carboxamide oxalate The product from Example 23, as the free base (0.330 g, 1 mmol) and triethylamine (0.15 mL, 1.05 mmol) were stirred in 10.0 mL tetrahydrofuran and cooled briefly in an ice bath. To the mixture was added dropwise trimethylacetyl chloride (0.12 mL, 1 mmol) and the resulting mixture was stirred 18 h at room temperature and filtered, and the filtrate was evaporated to 0.384 g oil. Crystallization as the oxalate salt from 2-propanol provided 0.297 g colorless crystals. Mp 194° C. Mass spectrum, m$^+$=413. Anal ($C_{25}H_{37}N_5O_6$) theory C, 59.63; H, 7.41; N, 13.91; found C, 59.47; H, 7.62; N, 13.63.

EXAMPLE 34

Preparation of N-[2-($^4$-benzylaminocarbonylamino)-1-piperidinyl)ethyl]-1-($^2$-propyl)-1H-indazole-3-carboxamide oxalate The product from Example 23, as the free base (0.330 g, 1 mmol) was stirred in 8 mL tetrahydrofuran and cooled in an ice bath to 10° C. To the mixture was added dropwise benzyl isocyanate (0.12 mL, 1 mmol) and the resulting mixture was stirred 1.5 h at room temperature and evaporated to an oil. Crystallization as the oxalate salt from ethanol provided 0.319 g colorless crystals. Mp 168° C. Mass spectrum. m$^+$=463. Exact mass theory, 463.2821; found, 463.2838.

EXAMPLE 35

Preparation of N-[2-($^4$-phenylaminocarbonylamino)-1- piperidinyl)ethyl]-1-($^2$-propyl)-1H-indazole-3-carboxamide oxalate The product from Example 23, as the free base (0.330 g, 1 mmol) was stirred in 8 mL tetrahydrofuran and cooled in an ice bath to 10° C. To the mixture was added dropwise phenyl isocyanate (0.11 mL, 1 mmol) and the resulting mixture was stirred 1.5 h at room temperature and evaporated to an oil. Crystallization as the oxalate salt from ethanol provided 0.299 g colorless crystals. Mp 198° C. Mass spectrum, m$^+$=449. Anal ($C_{27}H_{34}N_6O_6$) theory C, 60.21; H, 6.36; N, 15.60; found C, 60.42; H, 6.60; N, 15.47.

EXAMPLE 36

Preparation of N-[2-(4-(4-fluorophenyaminocarbonylamino)-1-piperidinyl) ethyl]-1-($^2$-propyl)-1H-indazole-3-carboxamide oxalate The product from Example 23, as the free base (0.330 g, 1 mmol) was stirred in 8 mL tetrahydrofuran and cooled in an ice bath to 10° C. To the mixture was added dropwise 4-fluorophenyl isocyanate (0.11 mL, 1 mmol) and the resulting mixture was stirred 1.5 h at room temperature and filtered, and the filtrate was evaporated to an oil. Crystallization as the oxalate salt from ethyl acetate/methanol provided 0.147 g colorless crystals. Mp 158° C. Mass spectrum, m$^+$=466. Anal ($C_{27}H_{33}FN_6O_6$) theory C, 58.27; H, 5.98; N, 15.10; found C, 58.48; H, 6.23; N, 14.94.

EXAMPLE 37

Preparation of N-[(2-(4-(3-hydroxy-1-adamantylcarbonylamino)-1-piperidinyl)ethyl]-1-(2-propyl)-1H-indazole-3-carboxamide oxalate A mixture of 1.07 g (5.45 mmol) of 3-hydroxy-1-adamantylcarboxylic acid and 0.88 g (5.45 mmol) of 1,1'-carbonyldiimidazole in 10 mL of dimethylformamide was stirred for 2 hours at ambient temperature. To this solution was dropwise added 1.80 g (5.45 mmol) of the product of Example 23 in 7 mL of dimethylformamide. The reaction was stirred for 18 hours and then concentrated in vacuo, diluted with dichloromethane and solids removed by filtration. The crude product was purified by chromatography (silica, 9:1 dichloromethane-methanol) to provide 1.30 g (47%) of the desired product as a foam. Further treatment of the product with 0.23 g (2.62 mmol) of oxalic acid in 20 mL of ethanol provided, upon concentration of the solution, 1.51 g of the oxalate salt (LSN343031). $^1$H NMR (500 MHz, DMSO-$d_6$) d 8.51 (t, 1H), 8.19 (d, 1H), 7.9 (br s, 3H), 7.78 (d, 1H), 7.44 (t, 1H), 7.40 (d, 1H), 7.27 (t, 1H), 5.06 (m, 1H), 3.84 (m, 1H), 3.72 (m, 2H), 3.52 (m, 2H), 3.24 (br t, 2H), 3.07 (br t, 2H), 2.11 (br s, 2H), 1.82 (m, 4H), 1.64 (m, 6H), 1.55 (m, 10H), 1.48 (br s, 2H).

EXAMPLE 38

Preparation of N-[2-(4-(4-hydroxy-1-adamantylcarbonylamino)-1-piperidinyl)ethyl]-1-(2-propyl)-1H-indazole-3-carboxamide oxalate A mixture of 0.50 g (2.55 mmol) of 4-hydroxy-1-adamantylcarboxylic acid and 0.44 g (2.71 mmol) of 1,1'-carbonyldiimidazole in 10 mL of dimethylformamide was stirred for 2 hours at ambient temperature. To this solution was dropwise added 0.90 g (2.75 mmol) of the product of Example 23 in 7 mL of dimethylformamide. The reaction was stirred for 18 hours and then concentrated in vacuo, diluted with dichloromethane and solids removed by filtration. The crude product was purified by chromatography (silica, 9:1 dichloromethane-methanol) to provide 0.71 g (55%) of the desired product as a foam. Further treatment of 500 mg of the product with 88 mg of oxalic acid in 15 mL of ethanol provided, upon concentration of the solution, 580 mg of the oxalate salt (LSN343032). $^1$H NMR (300 MHz, DMSO-$d_6$) d 8.47 (t, 1H), 8.11 (d, 1H), 7.75 (d, 1H), 7.40 (t, 1H), 7.28 (d, 1H), 7.21 (t, 1H), 6.3 (br s, 3H), 5.04 (m, 1H), 3.74 (m, 1H), 3.59 (m, 3H), 3.40 (m, 2H), 3.13 (m, 2H), 2.95 (m, 2H), 1.95 (d, 2H), 1.69 (m, 13H), 1.47 (d, 6H), 1.25 (d, 2H).

Treatment

Representative compounds of the present invention have been biologically tested to demonstrate their interaction with the 5-HT$_4$ receptor. The test was carried out in esophagus smooth muscle, freshly removed from male Wistar rats weighing 250–300 g each. The rats were killed by cervical dislocation, and the esophagus was removed and dissected free of connective tissue. The esophagi were used as longitudinal preparations—obtaining two preparations from each animal. The tissues were tied with thread at each end with the lower end being tied to a stationary glass rod and the upper end to a force transducer.

Tissues were mounted in organ baths containing 10 mL of modified Krebs' solution of the following composition (millimolar) NaCl 118.2; KCl 4.6; CaCl$_2$.2H$_2$O 1.6; KH$_2$PO$_4$ 1.2; MgSO$_4$ 1.2; dextrose 10.0; and NaHCO$_3$ 24.8. Tissue bath solutions were maintained at 37° C. and aerated with 95% O$_2$-5% CO$_2$. Tissues were placed under optimum resting force, 1 g, and were allowed to equilibrate for 1 hr before exposure to drugs. Isometric contractions were recorded as changes in grams of force on the Modular Instruments Inc. (Malvern, Pa.) model M4000 data acquisition system with Sensotec (Columbus, Ohio) model MBL 5514-02 transducers.

For studies with partial agonists or antagonists, tissues were preincubated with vehicle or antagonist for 45 min. All drugs were prepared daily in deionized water and kept on ice during the course of the experiment. The tissues were contracted by incubation with $10^{-7}$–$10^{-5}$M carbamylcholine, and were relaxed by the addition of serotonin at $10^{-8}$–$10^{-10}$M, which treatment relaxed the tissue and reduced the contraction caused by carbamylcholine.

Addition of a compound of the present invention antagonized the serotonin response and reduced the observed relaxations of the tissue. Repeated tests of each compound at various concentrations were carried out, and the concentration that caused a two-fold shift of the relaxation curve was calculated. That concentration is reported here as the negative logarithm. In each case, the SEM of the data has been calculated and is shown below, as is the number of experiments carried out with each compound.

| Compound of Example No. | $-\text{Log } K_B$ |
| --- | --- |
| 1 | 7.5 ± .01 (4) |
| 2 | 8.0 ± .3 (9) |
| 4 | 8.1 ± .4 (3) |
| 6 | 8.2 ± .1 (5) |
| 8 | 8.8 ± .2 (15) |
| 10 | 7.7 ± .1 (3) |
| 12 | 8.0 ± .6 (4) |
| 14 | 7.6 ± .2 (7) |
| 16 | 8.0 ± .3 (6) |
| 18 | 7.5 ± .4 (4) |
| 20 | 7.3 ± .2 (5) |
| 22 | 8.0 ± .3 (4) |
| 23 | 6.8 ± 1 (4) |
| 24 | 7.9 ± .6 (4) |
| 25 | 8.6 ± .2 (8) |
| 26 | 8.4 ± .2 (8) |
| 27 | 9.9 ± .4 (6) |
| 28 | 8.3 ± .3 (4) |
| 29 | 8.5 ± .2 (3) |
| 30 | 7.8 ± .3 (4) |
| 31 | 7.7 ± .4 (4) |
| 32 | 8.6 ± .2 (5) |
| 33 | 8.5 ± .3 (3) |
| 34 | 8.3 ± .4 (3) |
| 35 | 8.0 ± .2 (3) |
| 36 | 7.6 ± .05 (3) |
| 37 | 8.9 |
| 38 | 8.7 |

The above data demonstrate that the compounds of the present invention have extremely high affinity for the 5-HT$_4$ receptor. Further, it has been found that the compounds of the present invention have a usefully long duration of action in vivo, particularly as compared to cisapride, a presently known compound with high affinity at the 5-HT$_4$ receptor. It is also remarkable that compounds of the present invention are markedly more potent in their affinities at the 5-HT$_4$ receptor than in other activities and at other receptors; the selectivity is often proved by concentration differences amounting to two or even more orders of magnitude to achieve the same binding potency.

Accordingly, the methods of the present invention are very potent in affecting the 5-HT$_4$ receptor, and particularly in providing an antagonist effect at that receptor. The methods of the present invention are carried out by administering a compound as described above in an effective dose to a subject in need of such an effect at the 5-HT$_4$ receptor, or in need of treatment or prophylaxis of a dysfunction or disorder of the 5-HT$_4$ receptor. An effective dose, in the contemplation of the present invention, is an amount of compound which is adequate to provide the desired effect, or to provide treatment for the disorder. The compounds are effective, in general, at quite low doses, and are effective over a substantial dosage range. Effective doses will normally fall within the range from about 0.001 to about 30 mg/kg/day of body weight. As usual in pharmaceutical treatments, the daily dose may be administered in a single bolus, or in divided doses, at the judgment of the physician in charge. A more preferred range of doses is from about 0.1 to about 3.0 mg/kg/day. It will be understood by the reader that the dose for a given subject is always to be set by the judgment of the attending physician, and that the dose is subject to modification based on the size of the patient, the lean or fat nature of the subject, the characteristics of the particular compound chosen, the intensity of the subject's symptoms or disease involvement, and perhaps psychological factors which may affect the subject's physiological responses.

The invention is effective in mammals which possess a $5\text{-HT}_4$ receptor; the preferred subject is the human.

As briefly mentioned above, a variety of physiological functions have been shown to be influenced by the $5\text{-HT}_4$ receptor. Accordingly, the methods of the present invention include methods of treatment or prophylaxis of pathologies of the central nervous system such as anxiety, pain, depression, schizophrenia, memory disorders, and dementia; pathologies of the gastrointestinal tract such as irritable bowel syndrome, nausea, gastroesophageal reflux disease, dyspepsia, gastrointestinal motility disorders, and constipation; cardiovascular disorders such as atrial fibrillation, arrhythmias and tachycardia; and genitourinary disorders such as urinary retention, urinary incontinence, and pain on urination. The dosage rates for the treatment of the foregoing disorders are those which have just been mentioned as effective for blocking the $5\text{-HT}_4$ receptor, since treatment or prophylaxis is obtained by activity at that receptor.

Pharmaceutical Compositions

It is customary to formulate pharmaceuticals for administration, to provide control of the dosage and stability of the product in shipment and storage, and the usual methods of formulation are entirely applicable to the compounds of Formula I. Such compositions, comprising at least one pharmaceutically acceptable carrier, are valuable and novel because of the presence of the compounds of Formula I therein. Although pharmaceutical chemists are well aware of many effective ways to formulate pharmaceuticals, which technology is applicable to the present compounds, some discussion of the subject will be given here for the convenience of the reader.

The usual methods of formulation used in pharmaceutical science and the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compound in total, depending on the desired dose and the type of composition to be used. The amount of the compound, however, is best defined as the effective amount, that is, the amount of each compound which provides the desired dose to the patient in need of such treatment. The activity of the compounds do not depend on the nature of the composition, so the compositions are chosen and formulated solely for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with numerous pores through which the drugs are pumped by osmotic action.

The following typical formulae are provided for the interest and information of the pharmaceutical scientist.

Formulation 1

Hard gelatin capsules are prepared using the following ingredients:

|  | Quantity (mg/capsule) |
| --- | --- |
| Example 27 | 20 mg |
| Starch, dried | 200 mg |
| Magnesium stearate | 10 mg |
| Total | 230 mg |

Formulation 2

A tablet is prepared using the ingredients below:

|  | Quantity (mg/capsule) |
| --- | --- |
| Example 28 | 10 mg |
| Cellulose, microcrystalline | 400 mg |
| Silicon dioxide, fumed | 10 mg |
| Stearic acid | 5 mg |
| Total | 425 mg |

The components are blended and compressed to form tablets each weighing 425 mg.

Formulation 3

Tablets, each containing 10 mg of active ingredient, are made as follows:

|  | Quantity (mg/capsule) |
| --- | --- |
| Example 8 | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

Formulation 4

Capsules, each containing 30 mg of active ingredient, are made as follows:

|  | Quantity (mg/capsule) |
| --- | --- |
| Example 11 | 30 mg |
| Starch | 59 mg |
| Microcrystalline cellulose | 59 mg |
| Magnesium stearate | 2 mg |
| Total | 150 mg |

The active ingredient, cellulose, starch, and magnesium stearate are blended, passed through a No. 45 mesh U.S. sieve, and filled into hard gelatin capsules in 150 mg quantities.

Formulation 5

Suppositories, each containing 5 mg of active ingredient, are made as follows:

|  | Quantity (mg/capsule) |
| --- | --- |
| Example 21 | 5 mg |
| Saturated fatty acid glycerides | 2,000 mg |
| Total | 2,005 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions, each containing 10 mg of active ingredient per 5 ml dose, are made as follows:

|  | Quantity (mg/capsule) |
| --- | --- |
| Example 6 | 10 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethylcellulose and syrup to form a smooth paste. The benzoic acid solution, flavor and color are diluted with a portion of the water and added, with stirring. Sufficient water is then added to produce the required volume.

Formulation 7

An intravenous formulation may be prepared as follows:

|  | Quantity (mg/capsule) |
| --- | --- |
| Example 32 | 10 mg |
| Isotonic saline | 1,000 ml |

We claim:

1. A method of antagonizing the 5-HT$_4$ receptor in the gastrointestinal tract or genitourinary tract comprising administering to a subject in need of such treatment an effective 5-HT$_4$ antagonizing amount of a compound of the formula

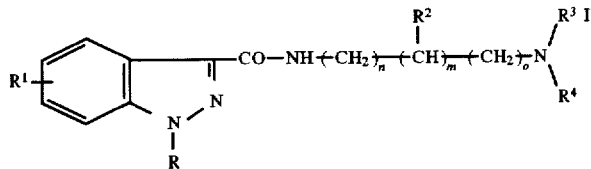

wherein:

R is hydrogen, C$_1$–C$_6$ alkyl, C$_3$–C$_6$ cycloalkyl;

R$^1$ is hydrogen, halo, C$_1$–C$_4$ alkyl, hydroxy, C$_1$–C$_4$ alkoxy or alkylthio, cyano, trifluoromethyl, carboxamido, mono- or di(C$_1$–C$_4$ alkyl)carboxamido;

m, n and o are independently 0–5, provided that the sum of m, n and o is 2–5;

R$^2$ is hydrogen or C$_1$–C$_4$ alkyl;

R$^3$ and R$^4$ combine with the nitrogen atom to which they are attached to form 1-pyrrolidinyl, 1-piperidinyl or 1-hexamethyleneiminyl, substituted with phenyl, naphthyl, (phenyl or naphthyl)(C$_1$–C$_3$ alkyl), (phenyl or naphthyl)(C$_1$–C$_3$ alkanoyl), amino, mono- or di(C$_1$–C$_4$ alkyl)amino, or a group of the formula —NH—Y—R$^5$;

wherein a phenyl or naphthyl group is unsubstituted or substituted with 1–3 halo, C$_1$–C$_3$ alkyl or C$_1$–C$_3$ alkoxy groups;

Y is carbonyl, sulfonyl, aminocarbonyl or oxycarbonyl;

R$^5$ is C$_1$–C$_6$ alkyl, C$_3$–C$_8$ cycloalkyl, C$_6$–C$_{11}$ bicyclo- or tricycloalkyl, (phenyl or naphthyl)(C$_1$–C$_3$ alkyl), phenyl or naphthyl;

wherein a cycloalkyl, bicyclo- or tricycloalkyl, phenyl or naphthyl group is unsubstituted or substituted with 1–3 hydroxy, halo, C$_1$–C$_3$ alkyl or C$_1$–C$_3$ alkoxy groups;

or a pharmaceutically acceptable salt thereof.

2. A method of claim 1 wherein the compound is a compound wherein m+n+o is 2–4, and R is hydrogen or alkyl.

3. A method of claim 2 wherein the compound is N-[2-(4-(1-adamantylcarboxamido)-1-piperidinyl)ethyl]-1-(2-propyl)-1H-indazole-3-carboxamide or a pharmaceutically acceptable salt thereof.

4. A method of claim 1 where the subject is suffering from or susceptible to a gastrointestinal tract disorder.

5. A method of claim 4 where the gastrointestinal tract disorder is irritable bowel syndrome, nausea, gastroesophageal reflux disease, dyspepsia, gastrointestinal motility disorders, or constipation.

6. A method of claim 4 where the compound is N-[2-(4-(1-adamantylcarboxamido)-1-piperidinyl)ethyl]-1(2-propyl)-1H-indazole-3-carboxamide or a pharmaceutically acceptable salt thereof.

7. A method of claim 1 where the subject is suffering from a genitourinary disorder.

8. A method of claim 7 where the genitourinary disorder is urinary retention, urinary incontinence, or pain on urination.

9. A method of claim 7 where the compound is N-[2-(4-(1-adamantylcarboxamido)-1-piperidinyl)ethyl]-1-(2-propyl)-1H-indazole-3-carboxamide or a pharmaceutically acceptable salt thereof.

* * * * *